PIERIS BUSH
Filed April 5, 1974
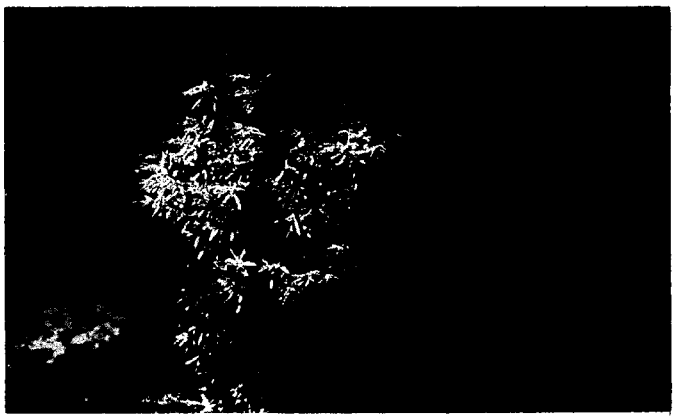
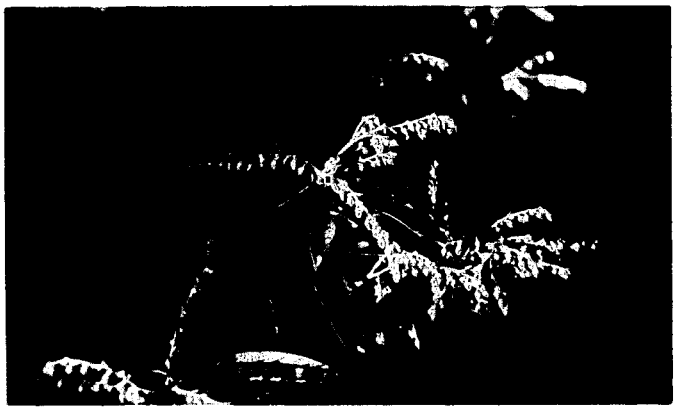
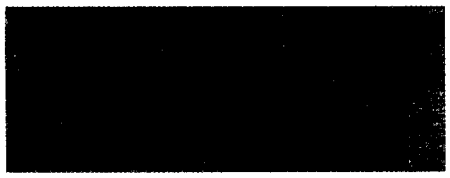
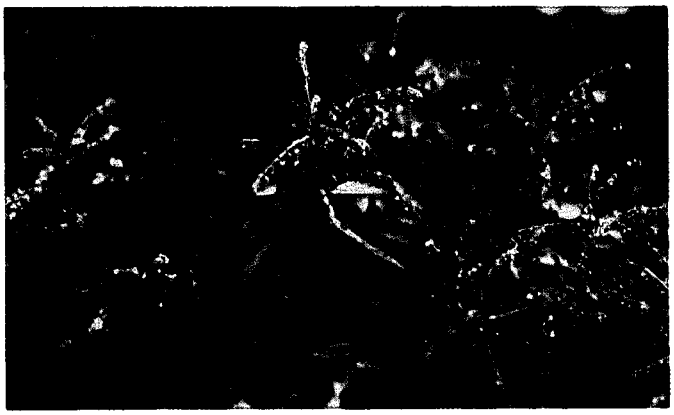

United States Patent

Plant Pat. 3,742

Patented July 15, 1975

3,742

PIERIS BUSH

Peter G. Brouwer, 24 Lester St.,
New London, Conn. 06320

Filed Apr. 5, 1974, Ser. No. 458,215

Int. Cl. A01h *5/00*

U.S. Cl. Plt.—54 1 Claim

ABSTRACT OF THE DISCLOSURE

A new variety of Pieris bush characterized by the branches of the inflorescence tending to the horizontal and in the fall and winter, the floral rachis, pedicels and calyces have a distinctive purplish red coloration when exposed to sunlight. The hybrid is sterile and does not develop seed capsules, and is a profuse, annual bloomer.

*Background of the Invention*

My new variety of Pieris bush originated as a seedling from a cross of *Pieris floribunda* (unpatented) and *Peris japonica* (unpatented) made by me at New London, Conn., during breeding efforts carried on by me since December 1960 with the object of producing a non-seeding variety having a better growth habit and which would otherwise retain the advantages of a popular plant such as Pieris. This seedling of Pieris floribunda appeared to have the characteristics that I was seeking and was therefore selected by me for propagation. Propagation of this new plant by cuttings has been carried on by me at Peter Brouwer's Nursery in New London, Conn., through several generations and all the scions have shown its novel characteristics are firmly fixed and hold true from generation to generation.

*Description of the Drawings*

My new variety of Pieris plant is illustrated by the accompanying photographic drawings. The hand color patch shows the true fall and winter color of the rachis, pedicels and calyces when they are exposed to sunlight. The upper view shows the full bush partly in the sunlight; the middle view shows details of the calyces, floral rachis and pedicels and shows that the branches of the inflorescence tend to the horizontal; and the lower view shows more detail.

*Description of the New Plant*

The following is a detailed description of the new variety of Pieris plan with color designation according to Nickerson's color fan blades.

THE PLANT

Origin:
Seedling.
Parentage:
Seed parent—*Pieris floribunda.*
Pollen parent—*Pieris japonica.*
Botanical Name: *Pieris floribunda*×*Pieris japonica.*
Form: Bush.
Shape: Globose.
Height: 1.2 m. (4 feet).
Twigs: Scattered simple hairs on young twigs.
Foliage—Leaves:
Quantity: Generous.
Size: 1½ to 2½ inches long; ¾ to 1½ inches wide.

Form: Ovate to oblong lanceolate.
Margin Type: Crenulate-serrulate, finely ciliate.
Texture: Leathery.
Color: Upper side—Dark green. Lower side—Lighter green. Not markedly different among presumptive parents and the hybrid.
Pubescence Distribution: Scattered glandular hairs prevalent on both sides.
Angle of Leaf Blade: Base to petiole 70°.

FLOWER BUDS

Form: Ovoid and angular.
Color: Fused corolla white. Fall and winter color of rachis, pedicels and calyces is deep purplish red when exposed to sunlight (10 R.P. 3/10 Nickerson color fan) and grading into green (leaf under surface color) when shaded.

FLOWERS

Blooming Period: Early spring—April in Northeastern States.
Quantity: Profuse, annual bloomer.
Size: Medium about 6 to 8 mm. in length.
Borne: In terminal panicles.
Petalage:
Color: Outer petal, body—white. Inside petal, body—white.

REPRODUCTIVE ORGANS

Stamens:
Number: 10.
Pollen: Pollen present but probably not functional.
Pistils: 1.

FRUIT

Appears to be sterile.

This new variety most resembles an intermediate to *Pieris floribunda* and *Pieris japonica* and is intermediate for most traits. Branches of the inflorescence tend to the horizontal compared to the erect form of *Pieris floribunda* and pendant form of *Pieris japonica.* An attractive feature in the fall and winter is the deep purplish red coloration of the floral rachis, pedicels and calyces. This new variety is easier to propagate from cuttings than *Pieris floribunda.* It is a vigorous grower when young, making a saleable plant faster than the parental species; however, growth of mature plants is not noticeably different. The new variety is less susceptible to laceburg than *Pieris japonica.* The hybrid is sterile and does not develop seed capsules, a trait which may account for its abundant annual production of flowers.

I claim:

1. A new and distinctive variety of Pieris plant substantially as herein shown and described, characterized by abundant seedless flowering, its branches of inflorescence tending to the horizontal, the deep purplish red coloration of the rachis, pedicels and calyces in the fall and winter, its easy propagation from cuttings, vigorous growing habits when young and less susceptibility to lacebug than *Pieris japonica.*

No references cited.

ROBERT E. BAGWILL, Primary Examiner